(12) United States Patent
Wilbertz et al.

(10) Patent No.: US 8,592,875 B2
(45) Date of Patent: Nov. 26, 2013

(54) SEMICONDUCTOR GAS SENSOR

(71) Applicant: Micronas GmbH, Freiburg (DE)

(72) Inventors: Christoph Wilbertz, Gundelfingen (DE); Heinz-Peter Frerichs, St. Peter (DE); Tobias Kolleth, Freiburg (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 13/683,324

(22) Filed: Nov. 21, 2012

(65) Prior Publication Data
US 2013/0126947 A1 May 23, 2013

Related U.S. Application Data

(60) Provisional application No. 61/564,597, filed on Nov. 29, 2011.

(30) Foreign Application Priority Data

Nov. 21, 2011 (DE) .......................... 10 2011 118 930

(51) Int. Cl.
*G01N 27/403* (2006.01)
(52) U.S. Cl.
USPC ............................ 257/253; 257/254; 257/414
(58) Field of Classification Search
USPC ............................ 257/253, 254, 414, E29.242
See application file for complete search history.

(56) References Cited

U.S. PATENT DOCUMENTS

| 5,137,461 | A | 8/1992 | Bindra et al. |
| 5,432,675 | A | 7/1995 | Sorimachi et al. |
| 5,545,589 | A | 8/1996 | Tomura et al. |
| 6,191,489 | B1 | 2/2001 | Igel et al. |
| 2009/0272175 | A1 * | 11/2009 | Frerichs et al. ............... 73/25.01 |

FOREIGN PATENT DOCUMENTS

| DE | 42 39 319 A1 | 4/1993 |
| DE | 199 07 168 C1 | 8/2000 |
| DE | 100 36 178 A1 | 2/2002 |
| DE | 10 2005 008 051 A1 | 8/2006 |
| EP | 1 103 808 A2 | 5/2001 |

* cited by examiner

*Primary Examiner* — Timor Karimy
(74) *Attorney, Agent, or Firm* — Muncy, Geissler, Olds & Lowe, PLLC

(57) ABSTRACT

A semiconductor gas sensor is provided that includes a semiconductor body with a passivation layer formed on a surface of thereof. A gas-sensitive control electrode is separated from a channel region by a gap or a control electrode is arranged as a first plate of a capacitor with a gap and a second plate of the capacitor is connected to a gate of the field effect transistor implemented as a Capacitively Controlled Field Effect Transistor. The control electrode has is connected to a reference voltage. A support area is provided with a first support structure and a second support structure. A contact area is provided on the surface of the semiconductor body. A first contact region has a frictional connection and an electrical connection with the control electrode and the second contact region has at least a frictional connection with the control electrode.

14 Claims, 2 Drawing Sheets

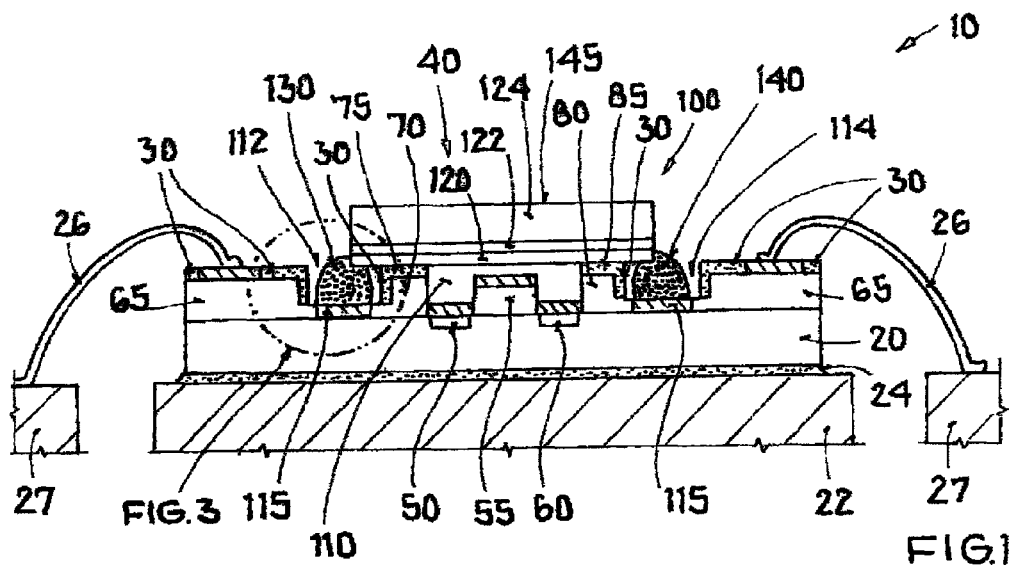
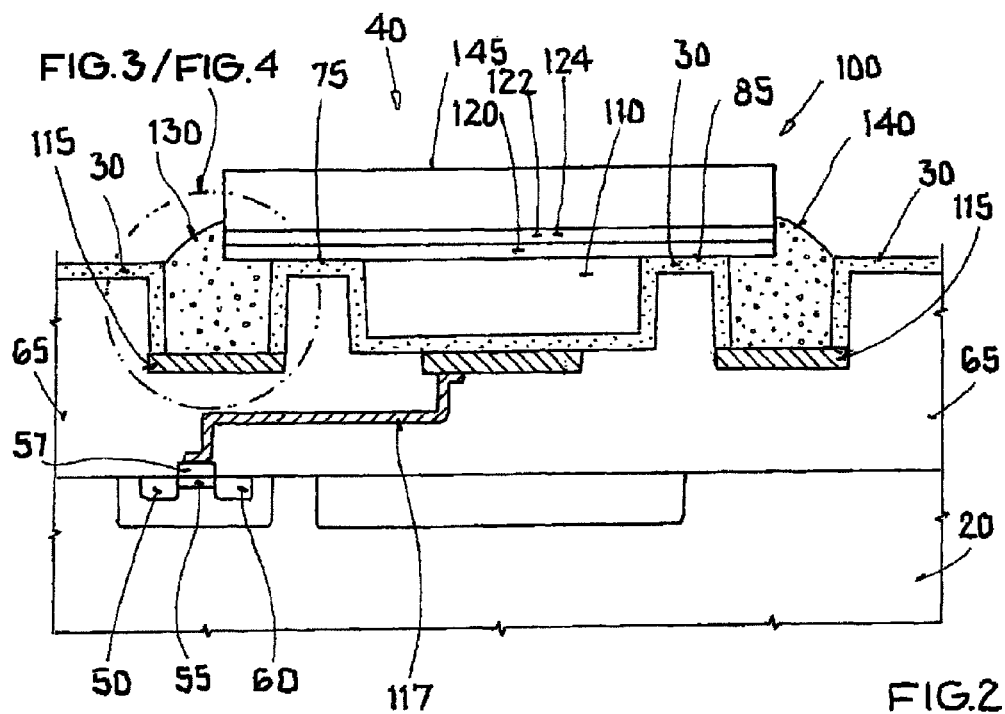

SEMICONDUCTOR GAS SENSOR

This nonprovisional application claims priority to German Patent Application No. DE 10 2011 118 930.4, which was filed in Germany on Nov. 21, 2011, and to U.S. Provisional Application No. 61/564,597, which was filed on Nov. 29, 2011, and which are both herein incorporated by reference.

BACKGROUND OF THE INVENTION

1. Field of the Invention

The invention relates to a semiconductor gas sensor.

2. Description of the Background Art

An FET moisture sensor is known from DE 100 36 178 A1. Here, the conductivity of the channel region is modulated by a Suspended Gate (SG). In addition, SGFET gas sensors are known from DE 42 39 319 C2, DE 10 2005 008 051 A, and EP 1 103 808 B1.

Moreover, additional mounting devices are known from DE 199 07 168 C1 (which corresponds to U.S. Pat. No. 6,191,489, and which is incorporated herein by reference), U.S. Pat. No. 5,545,589 A, U.S. Pat. No. 5,137,461 A, and U.S. Pat. No. 5,432,675 A.

A common characteristic of such MOS transistors with a control electrode spaced apart from the channel region by an air gap is that the control electrode and the semiconductor body generally are not implemented as a single piece. As a result, the control electrode must be connected to the associated transistor region by connecting components. Moreover, the control electrode has to be electrically connected.

SUMMARY OF THE INVENTION

It is therefore an object of the invention to provide a semiconductor gas sensor that advances the conventional art.

According to an embodiment of the invention, a semiconductor gas sensor on the basis of an integrated field effect transistor is provided, with a semiconductor body with a passivation layer formed on the surface of the semiconductor body, wherein the semiconductor gas sensor has a gas-sensitive control electrode separated from a channel region by a gap and is implemented as a Suspended Gate Field Effect Transistor (SGFET), or the control electrode is arranged as a first plate of a capacitor with a gap and a second plate of the capacitor is connected to a gate of the field effect transistor implemented as a Capacitively Controlled Field Effect Transistor (CCFET), and the control electrode has a semiconductor substrate layer with an overlying adhesive layer and a gas-sensitive layer overlying the adhesive layer, wherein the control electrode is connected to a reference voltage, and the surface of the gas-sensitive layer faces the channel region or the second plate, and in addition, a support area is provided with a first support structure with a first bearing region and with a second support structure with a second bearing region, wherein a contact area is provided on the surface of the semiconductor body and the support area adjoins the contact area, and the contact area has a first contact region and a second contact region, and comprises a first formation passing through the passivation layer and the first formation has a bottom surface with a conductive layer connected to the reference voltage and the first contact region has a frictional connection and an electrical connection with the control electrode by means of a first connecting component, and the second contact region has at least a frictional connection with the control electrode by means of a second connecting component, and the first connecting component at least partially fills the formation and connects the control electrode to the conductive layer.

The surface of the control electrode facing the channel region can also be referred to hereinafter as the inside surface, which is to say that the gas-sensitive layer is located on the inside surface. In this design, the gas-sensitive layer covers at least a portion of, preferably the entire, channel region in the case of the SGFET, or the counter electrode, which is to say the second plate, in the case of the CCFET, at a predetermined distance, wherein the distance determines the clear opening of the gap. The surface of the control electrode opposite the inside surface is called the outside surface or cover surface. Moreover, the term transistor area refers to an area that comprises the source region, the channel region, and the drain region.

It is an advantage that the control electrode, which in general is implemented as a layer stack, is not only connected mechanically, which is to say frictionally, to the semiconductor body by means of a first connecting component, but is also connected electrically to a reference voltage by means of the first connecting component. Investigations have shown that electrical connection by means of the first connecting component can replace an additional electrical contacting, for example by means of a bond wire. In this way, manufacture of the formation can be carried out as early as at the so-called wafer level and manufacture of the formation can easily be integrated into the process of manufacturing an integrated circuit. Manufacture of the gas sensors becomes more economical, and the reliability of the gas sensors increases. In addition, the overall height is reduced as compared to an implementation with a bond wire on the cover surface or outside surface of the control electrode. Investigations have shown that even a slight electrical conductivity of the first connecting component suffices to electrically connect the control electrode. It is preferred to make the contact resistance below 50 MOhm, extremely preferably below 1 MOhm. It is advantageous to implement the first connecting component and/or the second connecting component identically, and in particular as a conductive adhesive. It is sufficient here for the conductive adhesive, or at least the first connecting component, to have a conductivity above 1 S/m.

In other words, the SGFET or the CGFET can be referred to as an integrated component, wherein the first connecting component and/or the second connecting component represents a first part and the control electrode represents a second part of a third part formed underneath the passivation layer of an integrated component. An electrical signal connection exists between the different parts, which is to say that the individual parts of the integrated component stand in operative electrical connection with one another, and only in combination do they form the complete component.

In an embodiment, the control electrode is spaced apart from the contact area in the direction of the normal vector of the semiconductor surface, and covers the contact area. In this design, the distance between the control electrode and the contact area is determined, in particular, by the height of the first support structure and by the height of the second support structure, wherein it is preferred to make the height of the first support structure equal to the height of the second support structure. In this context, the height of the support structure is understood to mean the lateral length of the applicable support structure along the normal vector. In an especially preferred embodiment, the first bearing region and/or the second bearing region each comprise a plateau, wherein the plateaus are formed on the surface of the passivation layer and the control electrode rests on the plateaus. It is preferred here for the control electrode to rest only on the plateaus and to be held only by the first connecting component and/or the second connecting component, as well as to be connected only electrically with the reference voltage by means of one of the connecting component.

According to an embodiment, in addition to the first contact region, the second contact region also has a second formation passing through the passivation layer, with a bottom surface in each case. In addition, it is preferred for a conductive layer to be formed on the bottom surface of the second formation. It is preferred for the second connecting component to at least partially fill the second formation and to produce an electrical connection between the control electrode and the reference voltage in addition to the mechanical connection, by the means that the second connecting component, which possesses electrical conductivity, connects the control electrode to the conductive layer. It is further preferred to implement the two formations in the form of a trench or hole and to carry the formations through the dielectric layers of the individual trace levels. According to an alternative embodiment, it is preferred to implement a part of the lateral surface of the two formations with a conductive layer. Investigations have shown that a trace layer is suitable within the formation as is also a layer containing silicon, preferably a doped polysilicon layer with an overlying silicide layer. It is advantageous here to implement the silicide layer as tungsten silicide. In addition, it is preferred for the first connecting component and/or the second connecting component to completely fill the first formation or the second formation.

According to an embodiment, one frustoconical elevation, preferably a plurality of frustoconical elevations, is formed on the bottom surface. According to an enhancement, the elevations are designed to be conductive, and in particular it is preferred to implement the elevations as tungsten plugs. An advantage of the elevations is that the first connecting component and/or the second connecting component form an especially reliable mechanical and/or electrical connection with the formation and with the bottom surface, in particular. In other words, the tungsten plugs or the elevations increase the surface area that can be wetted by the two connecting component.

According to an embodiment, the first connecting component and the second connecting component are located solely underneath the control electrode and at the outside of the control electrode. In this way, the outside surface of the control electrode is not surrounded by one of the two connecting component, and the overall height of the gas sensor is reduced.

In another embodiment, it is especially advantageous for the first contact region to be directly adjacent to the first support structure. In this way, little area on the surface of the semiconductor is needed to create the gas sensor. In addition, it is advantageous to drive the SGFET or CCFET from an integrated circuit likewise located on the semiconductor body and to analyze the signals of the SGFET by means of the integrated circuit.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 shows a cross-sectional view of an SGFET semiconductor gas sensor;

FIG. 2 shows a cross-sectional view of a CCFET semiconductor gas sensor;

DETAILED DESCRIPTION

Figure 3:
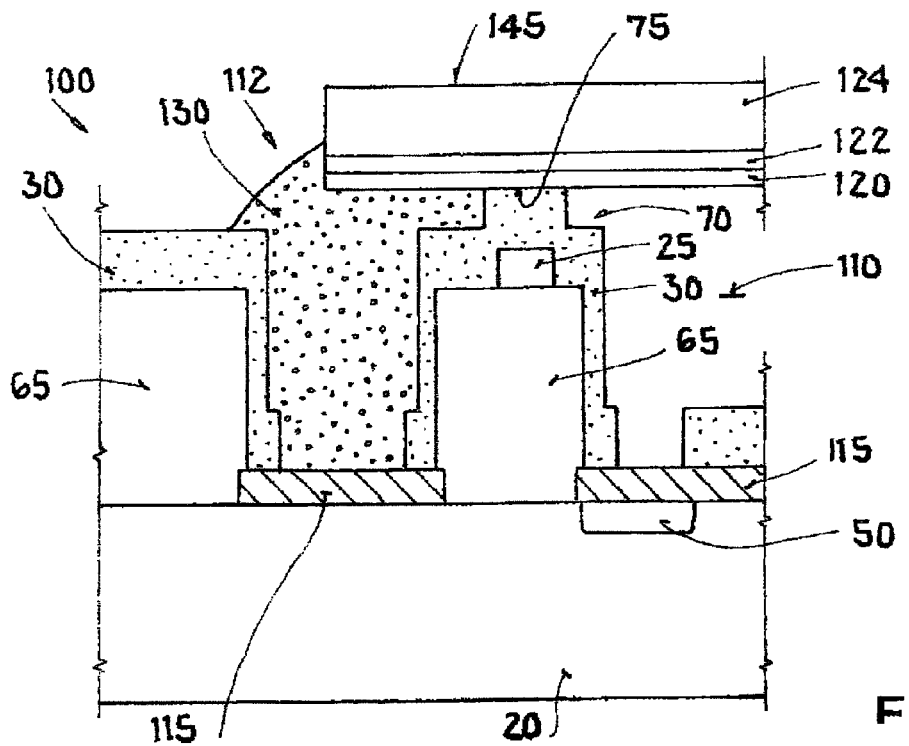
FIG. 3 shows a detailed view of a section of FIG. 1 and FIG. 2 according to a first embodiment.

The illustration in FIG. 1 shows a cross-sectional view of an SGFET semiconductor gas sensor, having a circuit package (not shown), a semiconductor gas sensor 10 integrated within the circuit package with a semiconductor body 20 with a passivation layer 30 formed on the surface, and a Suspended Gate Field Effect Transistor 40, also called SGFET for short, implemented in the semiconductor body 20, with a transistor area, a source area 50, a channel area 55, and a drain area 60. The semiconductor body 20 is secured to a carrier 22, also referred to as a lead frame, by means of an adhesive layer 24. Metal areas, so-called pads, are formed on the surface of the semiconductor body 20 in the uppermost trace level 25. The applicable pad is electrically connected to external, which is to say located outside of the circuit package, electrical connections by means of an associated bond wire 26 with an associated pin 27. The uppermost trace level 25 is covered by the passivation layer 30 except at the pads. Beneath the passivation layer 30, multiple oxide layers 65 are formed depending on the number of trace levels, wherein trace levels formed within the oxide layers are not depicted.

The SGFET has a support area with a first support structure 70 with a first bearing region 75, and a second support structure 80 with a second bearing region 85, wherein the transistor area is located on the surface of the semiconductor body 20 within the support area. The first bearing region 75 and the second bearing region 85 are arranged along the normal vector of the semiconductor surface above the transistor area, and are spaced apart from the transistor area.

A control electrode 100 is provided above the channel area 55, wherein the control electrode 100 spans the channel region 55 and rests upon the first bearing region 75 and the second bearing region 85, and a gap 110 is formed between the channel region 55 and the control electrode 100.

In its further progression the control electrode 100 partially covers a contact area formed on the surface of the semiconductor body 20, wherein the contact area comprises a first contact region with a first formation 112 and a second contact region with a second formation 114. The two formations 112, 114 preferably are designed as trench-like or hole-like structures, and in the present case extend through the passivation layer 30 located on the surface of the semiconductor body 20 and the oxide layers 65 located thereunder. A doped, electrically conductive polysilicon layer 115 with a silicide layer is located on the bottom of each of the two formations 112, 114.

Furthermore, the control electrode 100 is spaced apart from the contact area in the direction of the normal vector of the surface of the semiconductor body 20. Moreover, the control electrode 100 has a gas-sensitive layer 120 on the surface facing the channel region 55. On an adhesive layer 122, the gas-sensitive layer 120 is connected to a carrier material 124 generally made of a semiconductor material.

The support area is located on the surface of the semiconductor body 20 inside the contact area, wherein the contact area has a first contact region with the first formation 112 and a second contact region with the second formation 114, and the first contact region has both an electrical contact or connection as well as a frictional connection with the control electrode 100 by means of a first connecting component 130, which preferably is implemented as conductive adhesive. In this way, the control electrode 100 is connected to a reference voltage, which is not shown.

In addition, the second contact region is connected to the control electrode 100 by a second connecting component 140. It is beneficial if the second connecting component 140 is identical to the first connecting component 130. In this way, the process of manufacturing the gas sensor can be simplified and manufacturing costs can be saved. It must be noted that it is also sufficient, according to an alternative embodiment, for the second connecting component 140 to form only a frictional connection. Moreover, it is preferred for the first and second connecting component 130, 140 to be located beneath the control electrode 100 and at the outside of the control electrode 100, but not at the outside surface 145.

The illustration in FIG. 2 shows a cross-sectional view of a CCFET semiconductor gas sensor. In the following, only the differences from the illustration in FIG. 1 shall be explained. The transistor area is not formed beneath the control electrode 100 inside the gap 110, but rather at a different location. The gas-sensitive layer of the control electrode 100 now represents a first plate of a capacitor. The second plate of the capacitor is formed beneath the first plate in a bottom region of the gap 110, and is connected to a gate 57 of the field effect transistor by a trace 117. In addition, the second plate is covered with the passivation layer 30 and protected in this way from environmental influences. Now if the work function at the first plate of the capacitor changes, the voltage at the gate 57 of the field effect transistor changes as a result, and consequently also the conductivity in the channel region 55. Thus, the gate voltage of the field effect transistor is controlled capacitively.

The illustration in FIG. 3 shows a detailed view of a section of FIG. 1 and FIG. 2 according to a first embodiment. In the following, only the differences from the embodiments in the preceding figures shall be explained. It is a matter of course that the embodiments explained below can easily be transferred to the second contact area. The control electrode 100 partially covers the first formation 112. To produce the first formation 112, the oxide layers 65 preferably are removed by means of an anisotropic etching process, with the exception of the electrically conductive polysilicon layer 115 located beneath the oxide layer. The passivation layer 30 is formed at the lateral surfaces of the formation 112. This makes it evident that the first formation 112 has been applied by means of a first etching process prior to deposition of the passivation layer. Next, the polysilicon layer 115 is exposed in the bottom region of the formation 112 using a so-called pad window etching process. In an alternative embodiment that is not shown, the formation 112 can also be produced after deposition of the passivation layer 30. In this variation, no passivation layer 30 is formed on the lateral surfaces of the formation.

The first support structure 70 directly borders the first formation 112 or the first contact region. On its surface, the first support structure 70 has the bearing region 75 that is elevated in a mesa-like manner. The elevation is created through the creation of a trace in the uppermost trace level 25, beneath the passivation layer 30, and, together with the control electrode 100 resting in an interlocking manner on the bearing region 75, forms a fold. In order to reliably connect the control electrode 100 with the semiconductor body 20 in both a frictional manner and electrically, the first connecting component 130 completely fills the first formation 112 and the fold. In addition, the first connecting component 130 surrounds a part of the lateral surface of the control electrode 100 and a part of the passivation layer 30 on the surface of the semiconductor body 20. In this way, a very reliable and durable connection of the control electrode 100 with the semiconductor body 20 is formed through the first connecting component 130.

Figure 4:
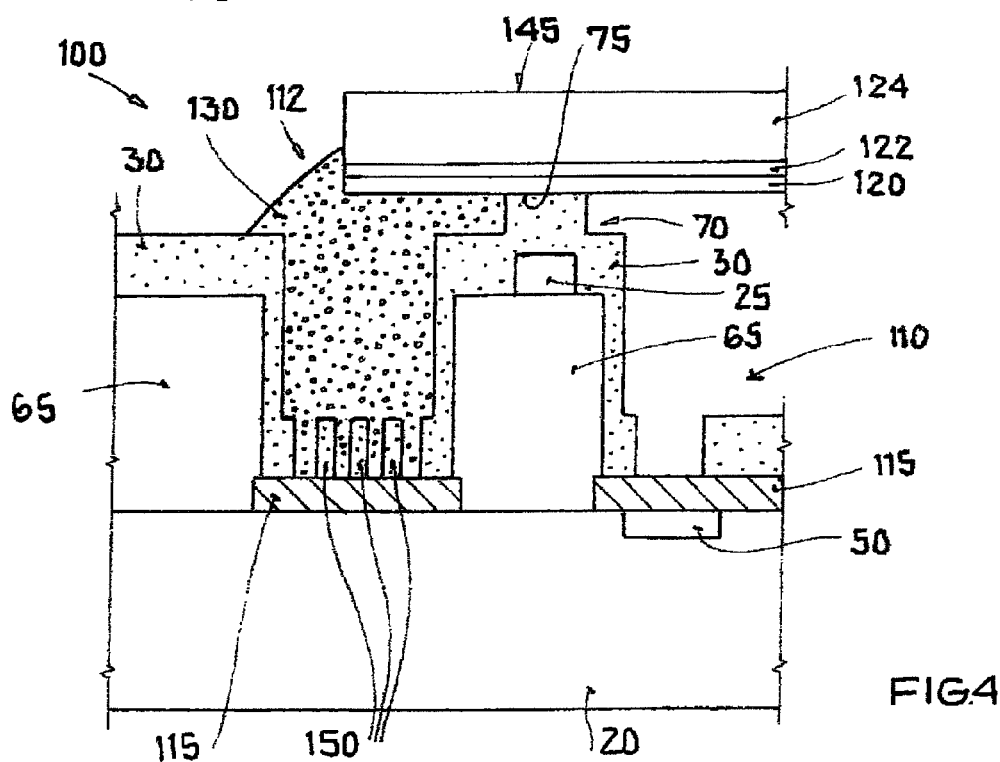
FIG. 4 shows a detailed view of a section of FIG. 1 and FIG. 2 according to a second embodiment.

The illustration in FIG. 4 shows a detailed view of a section of FIG. 1 and FIG. 2 according to a second embodiment. In the following, only the differences from the embodiments in the preceding figures shall be explained. A plurality of frustoconical elevations, which preferably are implemented as tungsten plugs 150, are arranged on the bottom surface or on the polysilicon layer 115. The tungsten plugs 150 form an interlocking and frictional connection with the base, which preferably is implemented as a silicide layer, most preferably as a tungsten silicide layer. The tungsten plugs 150 are each encased in the first connecting component 130. In this way, an especially strong and reliable connection is formed between the first connecting component 130 and the bottom region.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A semiconductor gas sensor comprising:
   a semiconductor body having a passivation layer formed on a surface of the semiconductor body;
   a gas-sensitive control electrode separated from a channel region by a gap and implemented as a Suspended Gate Field Effect Transistor or the control electrode being arranged as a first plate of a capacitor with a gap, and a second plate of the capacitor being connectable to a gate of the field effect transistor implemented as a Capacitively Controlled Field Effect Transistor, the control electrode having a semiconductor substrate layer with an overlying adhesive layer and a gas-sensitive layer overlying the adhesive layer, the control electrode being connectable to a reference voltage, and the surface of the gas-sensitive layer facing the channel region or the second plate;
   a support area having a first support structure with a first bearing region, and having a second support structure with a second bearing region; and
   a contact area formed on the surface of the semiconductor body,
   wherein the support area adjoins the contact area,
   wherein the contact area has a first contact region and a second contact region, the first contact region comprising a first formation passing through the passivation layer,
   wherein the first formation has a bottom surface with a conductive layer connectable to the reference voltage,
   wherein the first contact region has a frictional connection and an electrical connection with the control electrode via a first connecting component,
   wherein the second contact region has at least a frictional connection with the control electrode via a second connecting component, and
   wherein the first connecting component at least partially fills the formation and connects the control electrode to the conductive layer.

2. The semiconductor gas sensor according to claim 1, wherein the control electrode is spaced apart from the contact area in a direction of a normal vector of the semiconductor surface and covers the contact area at least partially.

3. The semiconductor gas sensor according to claim 1, wherein the second contact region has a second formation passing through the passivation layer, with a bottom surface, wherein a conductive layer is formed on the bottom surface, and wherein the first connecting component electrically connects the control electrode to the conductive layer.

4. The semiconductor gas sensor according to claim 3, wherein one frustoconical elevation is formed on the bottom surface.

5. The semiconductor gas sensor according to claim 4, wherein the elevation is implemented as a tungsten plug.

6. The semiconductor gas sensor according to claim 5, wherein a plurality of frustoconical elevations are formed on the bottom surface.

7. Semiconductor gas sensor according to claim 3, wherein the conductive layer contains silicon.

8. The semiconductor gas sensor according to claim 3, wherein the conductive layer is made of a doped polysilicon layer and a silicide layer.

9. The semiconductor gas sensor according to claim 1, wherein the first connecting component and the second connecting component contain a conductive adhesive.

10. The semiconductor gas sensor according to claim 1, wherein the first connecting component and the second connecting component are located solely underneath the control electrode and at an outside of the control electrode.

11. The semiconductor gas sensor according to claim 1, wherein the first contact region is directly adjacent to the first support structure.

12. The semiconductor gas sensor according to claim 3, wherein the first connecting component and/or the second connecting component completely fill the first formation and the second formation.

13. The semiconductor gas sensor according to claim 1, wherein the first bearing region and/or the second bearing region each comprise a plateau, wherein the plateaus are formed on the surface of the passivation layer, and wherein the control electrode rests on the plateaus.

14. The semiconductor gas sensor according to claim 1, wherein the control electrode rests only on the first bearing region and the second bearing region and is held only by the first connecting component and/or the second connecting component.

* * * * *